(12) United States Patent
Lim et al.

(10) Patent No.: US 12,654,004 B2
(45) Date of Patent: Jun. 16, 2026

(54) ACTIVATION DEVICE AND ODOR REMOVAL DEVICE INCLUDING SAME

(71) Applicant: IUCF-HYU (INDUSTRY-UNIVERSITY COOPERATION FOUNDATION HANYANG UNIVERSITY), Seoul (KR)

(72) Inventors: Tae Ho Lim, Seoul (KR); Jung Hyun Kim, Seoul (KR); Yeongtak Song, Seoul (KR); Jongbong Choi, Gyeonggi-do (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 1109 days.

(21) Appl. No.: 17/792,510

(22) PCT Filed: Sep. 28, 2020

(86) PCT No.: PCT/KR2020/013263
§ 371 (c)(1),
(2) Date: Jul. 13, 2022

(87) PCT Pub. No.: WO2021/066477
PCT Pub. Date: Apr. 8, 2021

(65) Prior Publication Data
US 2023/0063183 A1 Mar. 2, 2023

(30) Foreign Application Priority Data
Oct. 4, 2019 (KR) ........................ 10-2019-0123217

(51) Int. Cl.
*A61N 1/32* (2006.01)
*A61N 1/04* (2006.01)

(52) U.S. Cl.
CPC ........... *A61N 1/325* (2013.01); *A61N 1/0428* (2013.01)

(58) Field of Classification Search
CPC .. A61M 37/00; A61L 9/00; A61L 9/16; A61L 9/22
See application file for complete search history.

(56) References Cited

U.S. PATENT DOCUMENTS 5,829,066 A * 11/1998 Aibe ........................ E03D 9/052
4/213

FOREIGN PATENT DOCUMENTS

JP         5402947 B2      1/2014
KR   10-2006-0126788 A   12/2006
(Continued)

OTHER PUBLICATIONS

English translation of KR101407672B1 (Year: 2014).*
(Continued)

*Primary Examiner* — Nilay J Shah
(74) *Attorney, Agent, or Firm* — Sughrue Mion, PLLC

(57) ABSTRACT

Disclosed is an activation device. The activation device, which serves as a device coming into contact with an object to activate surrounding materials according to a dielectric barrier discharge principle, includes: a dielectric having a predetermined thickness and formed with an outer surface coming into contact with the object and an inner surface facing the outer surface; and an electrode provided inside the dielectric and having an outer surface facing the inner surface of the dielectric, wherein the outer surface of the electrode includes a contact area that comes into contact with the inner surface of the dielectric, and a non-contact
(Continued)

10 area that does not come into contact with the inner surface
of the dielectric.

9 Claims, 6 Drawing Sheets

(56)                    References Cited

FOREIGN PATENT DOCUMENTS

| KR | 101407672 | B1 | * | 6/2014 |
| KR | 10-2015-0049386 | A | | 5/2015 |
| KR | 10-2018-0003388 | A | | 1/2018 |
| KR | 10-1871983 | B1 | | 6/2018 |
| KR | 10-2019-0019806 | A | | 2/2019 |
| KR | 10-1978057 | B1 | | 5/2019 |

OTHER PUBLICATIONS

International Search Report of PCT/KR2020/013263 dated Mar. 26,
2021 [PCT/ISA/210].
Written Opinion of PCT/KR2020/013263 dated Mar. 26, 2021
[PCT/ISA/237].

* cited by examiner

【Fig. 1】
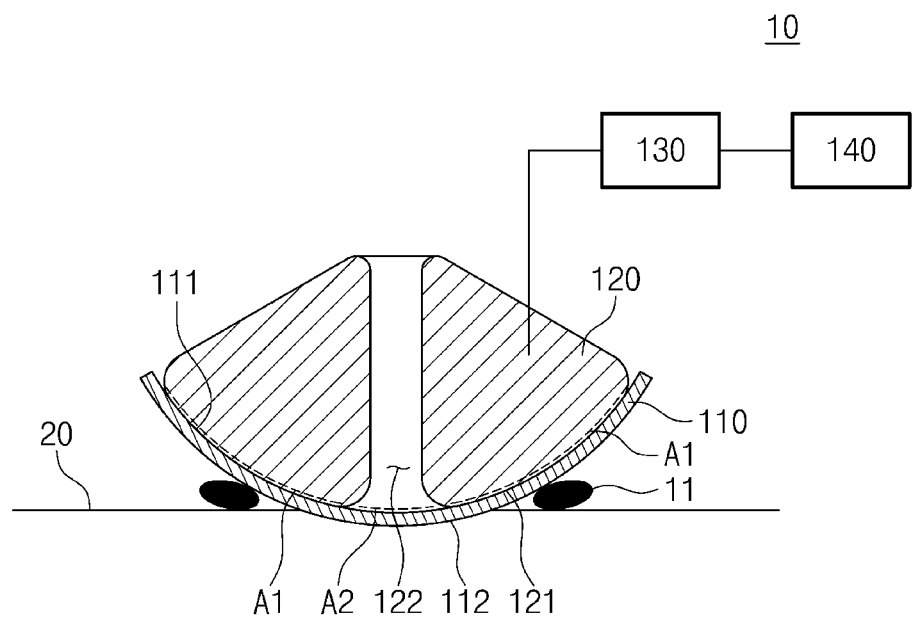
【Fig. 2】
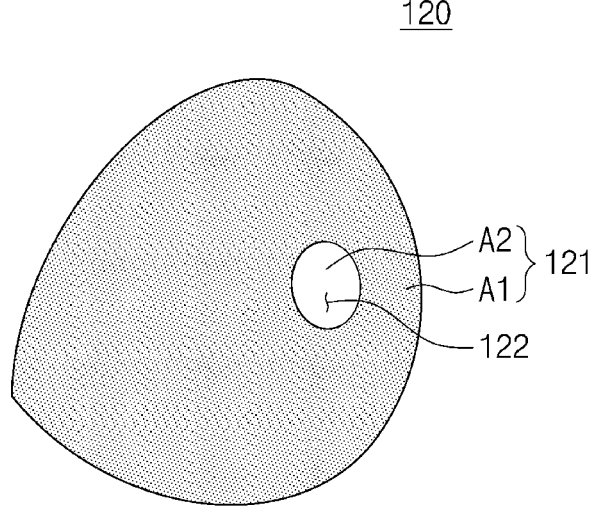

【Fig. 3】
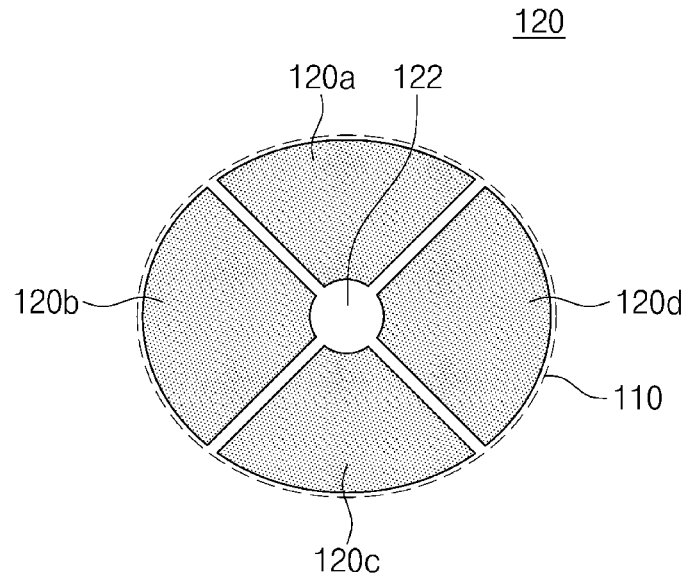
【Fig. 4】
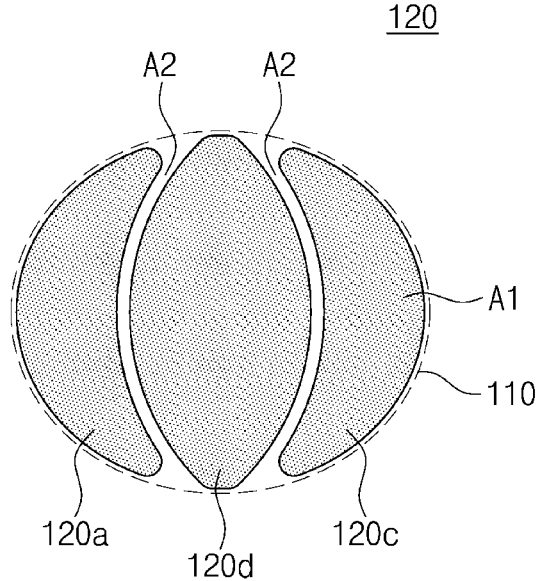

【Fig. 5】
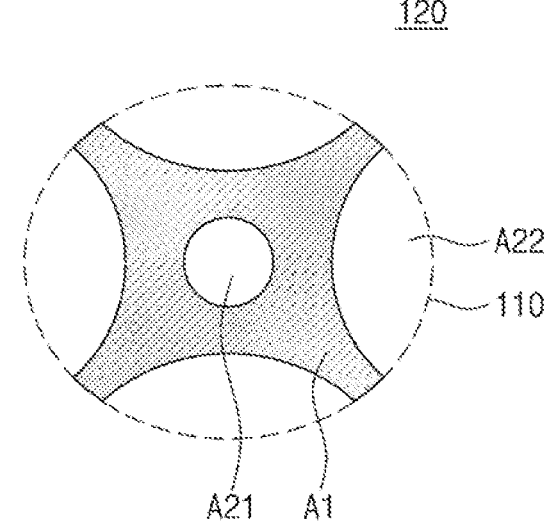
【Fig. 6】
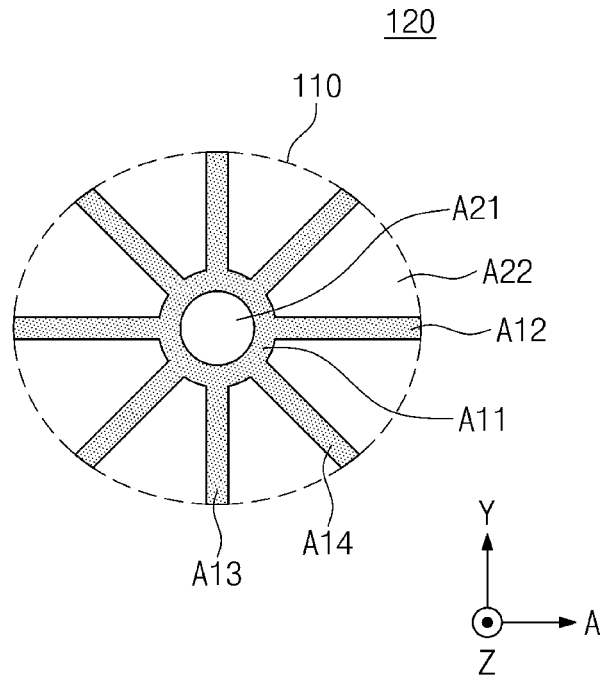

【Fig. 7】
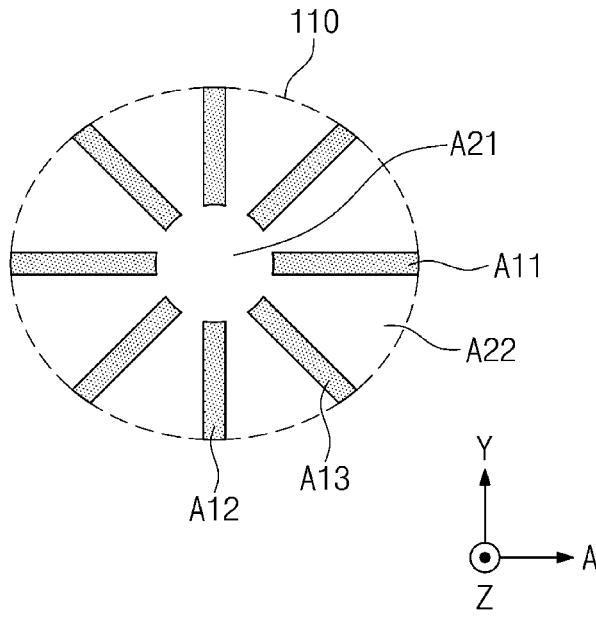
【Fig. 8】
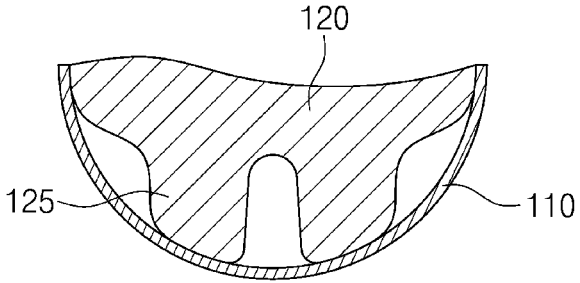

【Fig. 9】
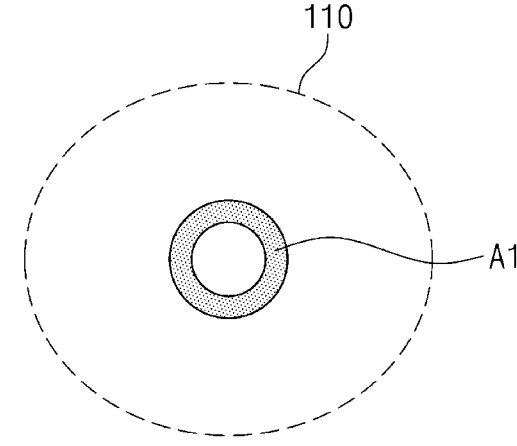
【Fig. 10】
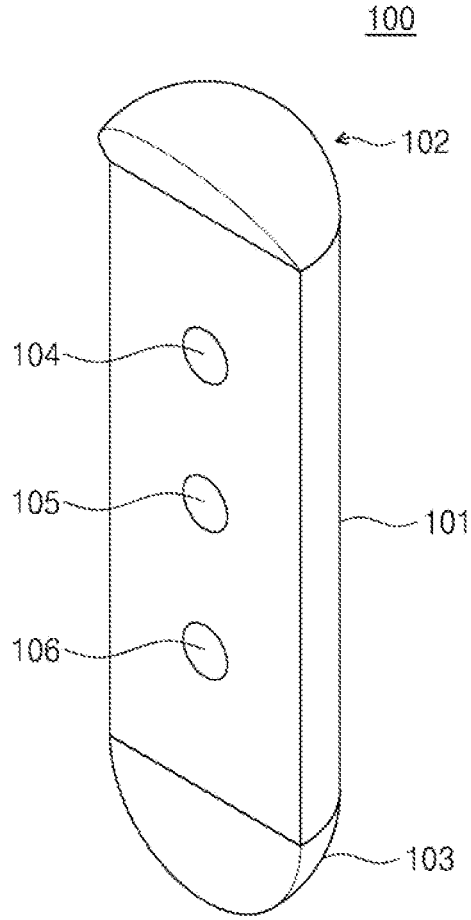

【Fig. 11】
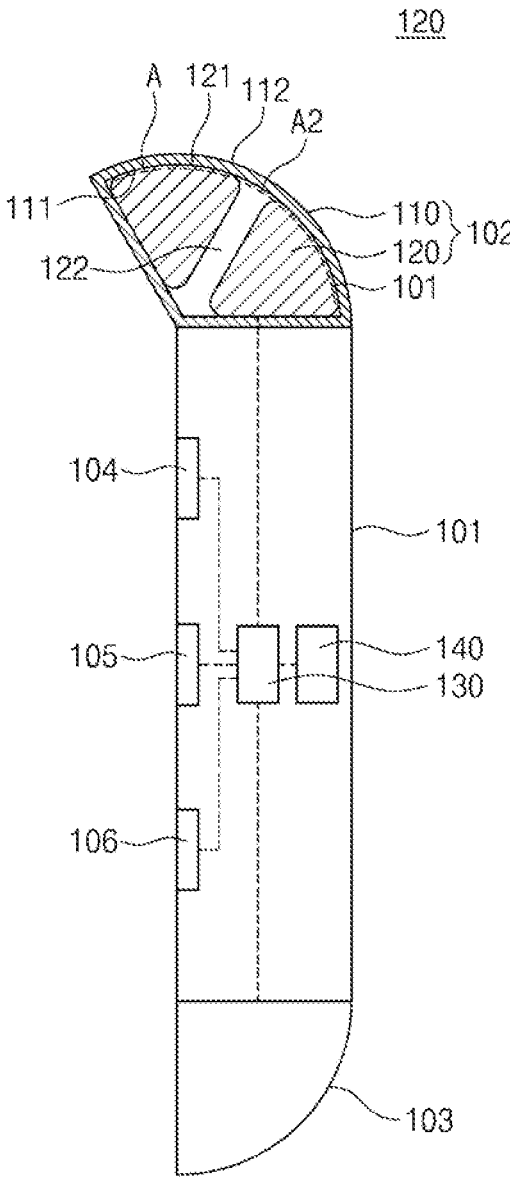

ACTIVATION DEVICE AND ODOR REMOVAL DEVICE INCLUDING SAME

CROSS REFERENCE TO RELATED APPLICATIONS

This application is a National Stage of International Application No. PCT/KR2020/013263, filed Sep. 28, 2020, claiming priority to Korean Patent Application No. 10-2019-0123217, filed Oct. 4, 2019.

BACKGROUND OF THE INVENTION

1. Field of the Invention

The present invention relates to an activation device and an odor removal device including the same, and more particularly, to an activation device and an odor removal device including the same to come into contact with an object so as to activate surrounding materials according to a dielectric barrier discharge principle.

2. Description of the Prior Art

The anti-aging-related market is rapidly growing due to socioeconomic changes such as the aging population, and market demands for a treatment device using a new energy source is very high to overcome limits of existing technologies.

For example, the transdermal drug delivery treatment is generally used by injection but has limitations due to causing of severe pain. As an alternative thereto, studies have been conducted on a treatment method using an activation device, and a treatment method using a jet, a treatment method by non-contact with the skin, and a treatment method by contact with the skin have been proposed.

The treatment method using a jet and the treatment method by non-contact have a limit in a therapeutic effect because energy of the active species delivered to the skin is low, and the treatment method by contact has a limit in that energy of the active species is low because a leakage current is generated in the area in contact with the skin.

SUMMARY OF THE INVENTION

The present invention provides an activation device capable of activating surrounding materials with high energy.

The present invention provides an odor removal device capable of suppressing odor without using chemical ingredients.

The activation device according to the present invention, which serves as a device coming into contact with an object to activate surrounding materials according to a dielectric barrier discharge principle, includes: a dielectric having a predetermined thickness, and formed with an outer surface coming into contact with the object and an inner surface facing the outer surface; and an electrode provided inside the dielectric and having an outer surface facing the inner surface of the dielectric, wherein the outer surface of the electrode includes a contact area that comes into contact with the inner surface of the dielectric, and a non-contact area that does not come into contact with the inner surface of the dielectric.

In addition, the non-contact area may be positioned in a central area of the outer surface of the electrode, and the contact area may surround the non-contact area.

In addition, the non-contact area may have a round or oval shape.

In addition, a plurality of contact areas may be provided and spaced apart from each other with the non-contact area therebetween.

In addition, the contact area may include: a ring-shaped first area; a second area extending from the first area in a first direction; a third area extending from the first area in a second direction perpendicular to the first direction; and a fourth area extending from the first area between the second area and the third area at a predetermined angle with respect to the first direction.

In addition, the contact area may include: a first area extending in a first direction; a second area spaced apart from the first area, and extending in a second direction perpendicular to the first direction; and a third area extending between the first area and the second area at a predetermined angle with respect to the first direction.

The odor removal device according to the present invention includes: a case; an activation device installed in the case and coming into contact with an object to activate surrounding materials according to a dielectric barrier discharge principle; and an odor sensing unit installed in the case, and coming into contact with the object to detect an odor, wherein the activation device may include: a dielectric having an outer surface exposed to an outside and provided as a curved surface; and an electrode positioned inside the dielectric in which power is applied to the electrode.

In addition, the dielectric may have a predetermined thickness, and have an inner surface facing the outer surface, wherein the outer surface of the electrode may include a contact area that comes into contact with the inner surface of the dielectric, and a non-contact area that does not come into contact with the inner surface of the dielectric.

In addition, the non-contact area may be positioned in a central area of the outer surface of the electrode, and the contact area may surround the non-contact area.

According to the present invention, the non-contact area of the electrode and the dielectric may be positioned at a contact point between the dielectric and the object, so that a current leakage can be minimized, and streamer with high energy may be generated along the boundary of the contact area between the electrode and the dielectric, so that the surrounding materials can be activated with high energy.

According to the present invention, organic matter may be removed and bacteria may be killed from the skin by using active species, so that odor-causing factors can be removed.

BRIEF DESCRIPTION OF THE DRAWINGS

The above and other objects, features, and advantages of the present invention will be more apparent from the following detailed description taken in conjunction with the accompanying drawings, in which:

FIG. 1 is a view schematically showing an activation device according to one embodiment of the present invention.

FIG. 2 is a sectional view showing a dielectric and an electrode according to one embodiment of the present invention.

FIG. 3 is a front view showing an electrode according to another embodiment of the present invention.

FIG. 4 is a front view showing an electrode according to still another embodiment of the present invention.

FIG. 5 is a front view showing an electrode according to still another embodiment of the present invention.

FIG. 6 is a front view showing an electrode according to still another embodiment of the present invention.

FIG. 7 is a front view showing an electrode according to still another embodiment of the present invention.

FIG. 8 is a sectional view showing an electrode according to still another embodiment of the present invention.

FIG. 9 is a front view showing a contact area between the electrode and the dielectric in FIG. 8.

FIG. 10 is a perspective view showing an odor removal device according to the embodiment of the present invention.

FIG. 11 is a sectional view showing the odor removal device of FIG. 10.

DETAILED DESCRIPTION OF THE EXEMPLARY EMBODIMENTS

An activation device according to the present invention, which serves as a device coming into contact with an object to activate surrounding materials according to a dielectric barrier discharge principle, includes: a dielectric having a predetermined thickness and formed with an outer surface coming into contact with the object and an inner surface facing the outer surface; and an electrode provided inside the dielectric, and having an outer surface facing the inner surface of the dielectric, wherein the outer surface of the electrode includes a contact area that comes into contact with the inner surface of the dielectric, and a non-contact area that does not come into contact with the inner surface of the dielectric.

Hereinafter, preferred embodiments of the present invention will be described in detail with reference to the accompanying drawings. However, the technical idea of the present invention is not limited to the exemplary embodiments described herein and may be embodied in other forms. Further, the embodiments are provided to enable contents disclosed herein to be thorough and complete and provided to enable those skilled in the art to fully understand the idea of the present invention.

In the specification herein, when one component is mentioned as being on other component, it signifies that the one component may be placed directly on the other component or a third component may be interposed therebetween. In addition, in drawings, thicknesses of layers and areas may be exaggerated to effectively describe the technology of the present invention.

In addition, although terms such as first, second and third are used to describe various components in various embodiments of the present specification, the components should not be limited by the terms. The above terms are used merely to distinguish one component from another. Accordingly, a first component referred to in one embodiment may be referred to as a second component in another embodiment. Each embodiment described and illustrated herein may also include a complementary embodiment. In addition, the term "and/or" is used herein to include at least one of the components listed before and after the term.

The singular expression herein includes a plural expression unless the context clearly specifies otherwise. In addition, it will be understood that the term such as "include" or "have" herein is intended to designate the presence of feature, number, step, component, or a combination thereof recited in the specification, and does not preclude the possibility of the presence or addition of one or more other features, numbers, steps, components, or combinations thereof. In addition, the term "connection" is used herein to include both indirectly connecting a plurality of components and directly connecting the components.

In addition, in the following description of the embodiments of the present invention, the detailed description of known functions and configurations incorporated herein will be omitted when it possibly makes the subject matter of the present invention unclear unnecessarily.

FIG. 1 is a view schematically showing an activation device according to one embodiment of the present invention. FIG. 2 is a sectional view showing a dielectric and an electrode according to one embodiment of the present invention.

Referring to FIGS. 1 and 2, an activation device 10 comes into contact with a surface of an object 20 to activate a surrounding material 11 at a contact point according to a dielectric barrier discharge principle. According to the embodiment, the activation device 10 may be used for transdermal drug delivery, anti-aging, skin care, skin disease treatment, and the like. The activation device 10 includes a dielectric 110, an electrode 120, a power source 130, and a control unit 140.

The dielectric 110 has a predetermined thickness, and has an inner surface 111 and an outer surface 112. The inner surface 111 and the outer surface 112 of the dielectric 110 may be provided as curved surfaces. The dielectric 110 may have a uniform thickness. The electrode 120 is positioned inside the dielectric 110, and the dielectric 110 is provided to surround at least one area of the electrode 120. The dielectric 110 may be provided as ceramic, and for example, may be configured to include at least one of alumina $(Al_2O_3)$, zirconia oxide $(ZrO_2)$, germanium (Ge), and cerium (Ce).

The electrode 120 is applied by power from the power source 140 under the control of the control unit 130. The electrode 120 is formed of a metal material. The electrode 120 is positioned inside the dielectric 110, and has an outer surface 121 facing the inner surface 111 of the dielectric 110. The outer surface 121 of the electrode 120 is provided as a curved surface corresponding to the inner surface 111 of the dielectric 110.

The outer surface 121 of the electrode 120 includes a contact area A1 in contact with the inner surface 111 of the dielectric 110, and a non-contact area A2 not in contact with the inner surface 111 of the dielectric 110. The non-contact area A2 may be positioned in a central area of the outer surface 121 of the electrode 120, and the contact area A1 may be provided to surround the non-contact area A1 around the non-contact area A2.

According to one example, the outer surface 121 of the electrode 120 may be formed with a hole or a groove 122 recessed inward to the electrode 120. The area formed with the hole or groove 122 is provided as the non-contact area A2 that does not come into contact with the inner surface 111 of the dielectric 110. The hole or groove 122 may have the same diameter toward an inner side of the electrode 120. On the contrary, the hole or groove 122 may have the diameter gradually decreased toward the inner side of the electrode 120.

The power is applied to the electrode 120 while a partial area of the dielectric 110 is in contact with the object 20. Due to the application of power, a streamer is generated along a periphery of the contact point between the dielectric 110 and the object 20. The streamer activates surrounding materials such as air. During the activation, active species, electrons, and ions are generated, ultraviolet rays and visible rays are emitted, and an electromagnetic field is generated.

According to the embodiment, the object 20 may include a body skin, and the activated material 11 removes organic matter, bacteria and the like from the skin and facilitates drug penetration.

Meanwhile, in the electrode 120, a current leakage occurs toward the object 20 from an area that is close to the object 20. The current leakage occurs at the contact point between the dielectric 110 and the object 20, in which the amount of current leakage is increased as a distance between the electrode 120 and the contact point is decreased.

The present invention the non-contact area A2 is formed on the outer surface of the electrode 120 at a position corresponding to the contact point, so that the occurrence of the current leakage is minimized.

Specifically, the dielectric 110 has the central area mainly coming into contact with the object 20, in which the non-contact region A2 of the electrode 120 is positioned in the central area of the dielectric 110. Accordingly, the current leakage to the central area of the dielectric 110 is minimized, and a high energy streamer is generated around the contact area boundary between the dielectric 110 and the object 20, so that the surrounding material can be activated with high energy.

FIG. 3 is a front view showing an electrode according to another embodiment of the present invention.

Referring to FIG. 3, the electrode 120 may be divided into a plurality of electrode pieces 120a to 120d. A groove is formed in each of the electrode pieces 120a to 120d. When the electrode pieces 120a to 120d are combined, the grooves are combined with each other, thereby forming one hole 122. The hole 122 is provided as the non-contact area A2. The present embodiment shows that the electrode 120 is divided into four electrode pieces 120a to 120d, however, the number of divided pieces may be variously changed.

FIG. 4 is a front view showing an electrode according to still another embodiment of the present invention.

Referring to FIG. 4, the electrode 120 may be divided into a plurality of electrode pieces 120a to 120c. The outer surface of the electrode 120 is provided with an interspace A2 between the electrode pieces 120a to 120c, and the interspace A2 is provided as a non-contact area. FIG. 5 is a front view showing an electrode according to still another embodiment of the present invention.

Referring to FIG. 5, a plurality of non-contact areas A21 and A22 may be formed on the outer surface of the electrode 120. Specifically, the non-contact areas A21 and A22 includes a first area A21 formed in a central area of the outer surface of the electrode 120, and a plurality of second area A22 spaced apart from each other along an outer peripheral area of the electrode 120. The first area A21 may have a circular or oval shape. The second area A22 may be recessed inward from the periphery of the electrode 120, and have an arc-shaped boundary line with the contact area A1. The first area A21 and the second area A22 and the second areas A22 are spaced apart from each other, and a contact area A1 is provided between the above areas. The streamer is generated along the boundary between the contact area A1 and the non-contact area A21 and A22.

FIG. 6 is a front view showing an electrode according to still another embodiment of the present invention.

Referring to FIG. 6, the contact area of the electrode 120 includes a first area A11, a second area A12, a third area A13, and a fourth area A14.

The first area A11 has a circular or oval ring shape and is positioned in the central area of the outer surface of the electrode 120. An inner space of the first area A11 is provided as the non-contact area A21. The second area A12 extends from both sides of the first area A11 by a predetermined length in a first direction X. The third area A13 extends from an upper end and a lower end of the first area A11 by a predetermined length in a second direction Y perpendicular to the first direction X. The third area A13 may have a length shorter than a length of the second area A12. The fourth area A14 slantingly extends from the first area A11 at a predetermined angle with respect to the first direction X, in each section between the second area A12 and the third area A13. Sections between the second to fourth areas A12 to A14 are provided as the non-contact area A22.

FIG. 7 is a front view showing an electrode according to still another embodiment of the present invention.

Referring to FIG. 7, the central area of the outer surface of the electrode 120 is provided as the non-contact region A21. The contact areas A11 to A13 are provided radially around the non-contact area A21. Specifically, the contact areas A11 to A13 includes a first area A11, a second area A12, and a third area A13.

The first area A11 extends from both sides of the non-contact area A21 by a predetermined length in the first direction X. The second area A12 extends from an upper end and a lower end of the non-contact area A21 by a predetermined length in the second direction Y perpendicular to the first direction X. The third area A13 slantingly extends from the non-contact area A21 at a predetermined angle with respect to the first direction X, in each section between the first area A21 and the second area A22. A section A22 between the first to third areas A11 to A13 is provided as a non-contact area.

FIG. 8 is a sectional view showing an electrode according to still another embodiment of the present invention. FIG. 9 is a front view showing a contact area between the electrode and the dielectric in FIG. 8.

Referring to FIGS. 8 and 9, a ring-shaped protrusion 125 is formed on the outer surface of the electrode 120, and the protrusion 125 comes into contact with the dielectric 110. Accordingly, the contact area A1 is formed as a ring shape.

As described above, the electrode 120 according to the embodiments of the present invention may be implemented such that the contact area A1 and the non-contact area A2 with the dielectric 110 have various shapes. In addition, the non-contact area is positioned at the contact point between the dielectric 110 and the object 20, so that a current leakage can be minimized, and the streamer with high energy are generated in various shapes along the boundary of the contact area, so that the surrounding material can be activated with high energy.

FIG. 10 is a perspective view showing an odor removal device according to the embodiment of the present invention. FIG. 11 is a sectional view showing the odor removal device of FIG. 10.

Referring to FIGS. 10 and 11, the odor removal device 100 detects the occurrence of odor, and generates active species in the odor-occurring area according to the dielectric barrier discharge principle. The active species remove organic matter and kill bacteria, so that odor-causing factors are removed. The odor removal device 100 according to the present invention may be used to remove bromhidrosis.

The odor removal device 100 includes a case 101, an activation device 102, an odor sensing unit 103, and a plurality of switches 104 to 106.

The case 101 as a body of the odor removal device 100 is accommodated therein with various devices such as a power source 130 and a control unit 140. The case 101 has a shape for enabling a user to hold the case comfortably by hand.

According to the embodiment, the case 101 may have one side provided as a curved surface, and the other side provided as a flat surface.

The activation device 102 may be installed on an upper end of the case 101. The activation device 102 comes into contact with the object 20 to generate active species according to the dielectric barrier discharge principle. The activation device 102 may use any one activation device 10 of the embodiments described with reference to FIGS. 1 to 9.

The odor sensing unit 103 may be provided at a lower end of the case 101. The odor sensing unit 103 is exposed to the outside, and comes into direct contact with the object 20 to detect the odor generated from the object 20. The odor sensing unit 103 may detect the odor caused by fatty organic matter excreted in sweat and bacteria.

A plurality of switches 104 to 106 are provided, and exposed to the outside of the case 101. One switch 104 may be used for controlling an on/off state of the odor removal device 100. Another switch 105 may be used as a switch for controlling the application of power to the electrode 120. The other switch 106 may be used as a switch for controlling the application of power to the odor sensing unit 103.

Although the present invention has been described in detail with reference to the exemplary embodiments, the present invention is not limited to the specific embodiments and will be interpreted by the following claims. In addition, it will be apparent that a person having ordinary skill in the art may carry out various deformations and modifications for the embodiments described as above within the scope without departing from the present invention.

The activation device according to the present invention may be used for transdermal drug delivery, anti-aging, skin care, skin disease treatment, and the like.

What is claimed is:

1. An activation device coming into contact with an object to activate surrounding materials according to a dielectric barrier discharge principle, the activation device comprising:

a dielectric having a predetermined thickness and formed with an outer surface coming into contact with the object and an inner surface facing the outer surface; and an electrode provided inside the dielectric and having an outer surface facing the inner surface of the dielectric, wherein a thickness of the electrode gradually increases from an edge region to a center region and a hole or a groove is formed inwardly from the outer surface of the electrode, wherein a region of the outer surface of the electrode where the hole or groove is formed is a non-contact region that does not contact the inner surface of the dielectric, and a remaining region is a contact region that is in contact with the inner surface of the dielectric.

2. The activation device of claim 1, wherein the non-contact area is positioned in a central area of the outer surface of the electrode, and the contact area surrounds the non-contact area.

3. The activation device of claim 1, wherein the non-contact area has a circular or oval shape.

4. The activation device of claim 1, wherein the contact area is provided with a plurality of contact areas spaced apart from each other with the non-contact area therebetween.

5. The activation device of claim 1, wherein the contact area includes:

a ring-shaped first area;

a second area extending from the first area in a first direction;

a third area extending from the first area in a second direction perpendicular to the first direction; and a fourth area extending from the first area between the second area and the third area at a predetermined angle with respect to the first direction.

6. The activation device of claim 1, wherein the contact area includes:

a first area extending in a first direction;

a second area spaced apart from the first area and extending in a second direction perpendicular to the first direction; and a third area extending between the first area and the second area at a predetermined angle with respect to the first direction.

7. An odor removal device comprising:

a case;

an activation device installed in the case and coming into contact with an object to activate surrounding materials according to a dielectric barrier discharge principle; and an odor sensing unit installed in the case and coming into contact with the object to detect an odor, wherein the activation device includes:

a dielectric having an outer surface exposed to an outside and provided as a curved surface and an inner surface facing the outer surface; and an electrode positioned inside the dielectric in which power is applied to the electrode, and having an outer surface facing the inner surface of the dielectric, wherein a thickness of the electrode gradually increases from an edge region to a center region and a hole or a groove is formed inwardly from the outer surface of the electrode, wherein a region of the outer surface of the electrode where the hole or groove is formed is a non-contact region that does not contact the inner surface of the dielectric, and a remaining region is a contact region that is in contact with the inner surface of the dielectric.

8. The odor removal device of claim 7, wherein the non-contact region has a circular or oval shape.

9. The odor removal device of claim 7, wherein the non-contact region is positioned in a central area of the outer surface of the electrode, and the contact area surrounds the non-contact area.

* * * * *